United States Patent
Foskey

(10) Patent No.: US 10,507,461 B2
(45) Date of Patent: Dec. 17, 2019

(54) SELECTIVE CATALYSTS FOR SPINETORAM PRODUCTION

(71) Applicant: Dow AgroSciences LLC, Indianapolis, IN (US)

(72) Inventor: Takiya J. Foskey, Midland, MI (US)

(73) Assignee: Dow AgroSciences LLC, Indianapolis, IN (US)

(*) Notice: Subject to any disclaimer, the term of this patent is extended or adjusted under 35 U.S.C. 154(b) by 0 days.

(21) Appl. No.: 15/444,793

(22) Filed: Feb. 28, 2017

(65) Prior Publication Data

US 2017/0252735 A1 Sep. 7, 2017

Related U.S. Application Data

(60) Provisional application No. 62/303,407, filed on Mar. 4, 2016.

(51) Int. Cl.
| | |
|---|---|
| *B01J 31/22* | (2006.01) |
| *B01J 31/24* | (2006.01) |
| *A01N 43/22* | (2006.01) |
| *C07H 17/08* | (2006.01) |

(52) U.S. Cl.
CPC .............. *B01J 31/22* (2013.01); *A01N 43/22* (2013.01); *B01J 31/24* (2013.01); *B01J 31/249* (2013.01); *B01J 31/2476* (2013.01); *C07H 17/08* (2013.01)

(58) Field of Classification Search
CPC ........ B01J 31/22; B01J 31/2476; B01J 31/24; B01J 31/249; C07H 17/08; A01N 43/22
USPC .......................................................... 536/7.1
See application file for complete search history.

(56) References Cited

U.S. PATENT DOCUMENTS 7,683,161 B2 * 3/2010 Podhorez ............... C07H 17/08
536/16.8

OTHER PUBLICATIONS

Graf et al. Ligand Effects in the Catalytic Hydrogenation of Carbon Dioxide to Formic Acid Using in situ Catalysts Formed from [ (( cod)Rh(μ-Cl))2] and Monodentate and Bidentate Phosphorus Ligands. Chem. Ber. 129:91-96, 1996. (Year: 1996).*

Gennari et al. Rhodium-catalyzed asymmetric reactions with a dynamic library of chiral tropos phosphorus ligands. Pure Appl. Chem., vol. 78, No. 2, pp. 303-310, 2006. (Year: 2006).*

Hou et al. Highly Efficient Rh(I)-Catalyzed Asymmetric Hydrogenation of Enamines Using Monodente Spiro Phosphonite Ligands.J. Am. Chem. Soc. 2006, 128, 11774-11775. (Year: 2006).*

Raoufmoghaddam et al. Chemo- and Regioselective Homogeneous Rhodium-Catalyzed Hydroamidomethylation of Terminal Alkenes to N-Alkylamides. ChemSusChem 2013, 6, 1759-1773. (Year: 2013).*

* cited by examiner

*Primary Examiner* — Yih-Horng Shiao

(57) ABSTRACT

This invention is based on the discovery that homogeneous catalysts, $[Rh(C_2H_4)_2Cl]_2$ and/or $[Rh(COD)_2][BF_4]$, can be used to produce spinetoram in higher yields at lower catalyst loadings as compared to previous methodologies. In addition, one or more phosphorus ligand donors can also be added to further increase yields/efficiency. The methods and/or systems provided herein enable cost-effective ways to produce spinetoram in large quantity with relatively simple procedures.

14 Claims, No Drawings

SELECTIVE CATALYSTS FOR SPINETORAM PRODUCTION

CROSS REFERENCE TO RELATED APPLICATIONS

This application claims priority under 35 U.S.C. § 119 of U.S. Provisional Patent Application Ser. No. 62/303,407, filed Mar. 4, 2016, which is hereby incorporated by reference in its entirety.

BACKGROUND OF THE INVENTION

Spinetoram is the common name for a mixture of (2R,3aR,5aR,5bS,9S,13S,14R,16aS,16bR)-2-(6-deoxy-3-O-ethyl-2,4-di-O-methyl-α-L-mannopyranosyloxy)-13-[(R2R,5S,6R)-5-(dimethylamino)tetrahydro-6-methylpyran-2-yloxy]-9-ethyl-2,3,3a,4,5,5a,5b,6,9,10,11,12,13,14,16a,16b-hexadecahydro-14-methyl-1H-as-indaceno[3,2-d]oxacyclododecine-7, 15-dione (also known as "dihydro-Et-J"), and (2R,3aR,5aS,5bS,9S,13S,14R,16aS,16bS)-2-(6-deoxy-3-O-ethyl-2,4-di-O-methyl-α-L-mannopyranosyloxy)-13-R2R,5S,6R)-5-(dimethylamino)tetrahydro-6-methylpyran-2-yloxyl-9-ethyl-2,3,3a,5a,5b,6,9,10,11,12,13,14,16a,16b-tetradecahydro-4,14-dimethyl-1H-as-indaceno[3,2-d]oxacyclododecine-7,15-dione (also known as "Et-L").

Spinetoram can be generated by hydrogenation of the mixture of Et-J and Et-L. U.S. Pat. No. 6,011,981 provides an example synthesis of 5,6-dihydro spinosyn J (example F27) using Wilkinson's catalyst (tris(triphenylphosphine)rhodium(I) chloride (Rh(PPh$_3$)$_3$Cl)) in 7 mole percent (mol %) loading. However, this methodology requires elevated temperature, and the yield needs further improvement. In addition, U.S. Pat. No. 7,683,161 provides certain heterogeneous catalysts for spinetoram synthesis. However, that methodology requires a relative high loading of catalysts. Both U.S. Pat. Nos. 6,011,981 and 7,683,161 are hereby incorporated by reference in their entireties.

Thus, there remains a need for developing new efficient catalysts for spinetoram production with high yields.

SUMMARY OF THE INVENTION

This invention is based on the discovery that a homogeneous catalyst of di-μ-chlorotetraethylene dirhodium(I) [Rh(C$_2$H$_4$)$_2$Cl]$_2$ and/or [Rh(COD)$_2$][BF$_4$] can be used to produce spinetoram by achieving higher yields at lower catalyst loadings as compared to previous methodologies. In addition, one or more phosphorus ligand donors can also be added to further increase yields/efficiency. The catalysts, methods, and/or systems provided herein enable cost-effective ways to produce spinetoram in large quantity with relatively simple procedures.

In one aspect, provided is a process for producing spinetoram. The process comprises hydrogenating a mixture of 3'-O-ethyl spinosyn J and 3'-O-ethyl spinosyn L, in the presence of a homogeneous catalyst selected from the group consisting of [Rh(C$_2$H$_4$)$_2$Cl]$_2$, [Rh(COD)$_2$][BR$_4$], [(COD)RhCL]$_2$, [Rh(COD)$_2$][OTs], and combinations thereof, at a temperature between 15° C. and 100° C. with a hydrogen gas pressure between 5 pounds per square inch gauge (psig) and 200 psig.

In one embodiment, the homogeneous catalyst is selected from the group consisting of [Rh(C$_2$H$_4$)$_2$Cl]$_2$, [Rh(COD)$_2$][BF$_4$], and combination thereof. In another embodiment, the method further comprises adding a phosphorus ligand donor.

In a further embodiment, the phosphorus ligand donor comprises tris(3,5-dimethylphenyl)phosphine. In another further embodiment, the phosphorus ligand donor is selected from the group consisting of

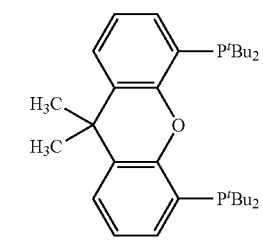

L31

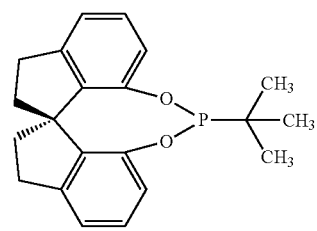

L16

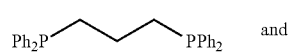

and

L23

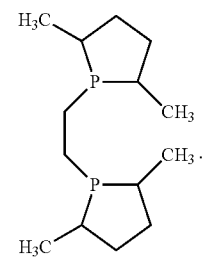

L27

In another embodiment, the temperature is between 25° C. and 80° C., between 25° C. and 50° C.; between 40° C. and 70° C.; or between 30° C. and 65° C. In another embodiment, the temperature is about 30° C., 45° C., or 65° C. In another embodiment, the hydrogen gas pressure is between 50 psig and 200 psig; between 60 psig and 150 psig; between 100 psig and 180 psig; or between 140 psig and 160 psig. In another embodiment, the hydrogen gas pressure is about 60 psig or 150 psig. In another embodiment, the yield of spinetoram is about or greater than 75%, 80%, 85%, 90%, or 95%. In another embodiment, the catalyst loading is between 0.01 mol % and 2 mol %; between 0.05 mol % and 1 mol %; between 0.02 mol % and 0.1 mol %; or between 0.1 mol % and 0.5 mol %.

In another aspect, provided is a system for producing spinetoram comprising a homogeneous catalyst selected from the group consisting of [Rh(C$_2$H$_4$)$_2$Cl]$_2$, [Rh(COD)$_2$][BF$_4$], [(COD)RhCL]$_2$, [Rh(COD)$_2$][OTs], and combinations thereof. In one embodiment, the homogeneous catalyst is selected from the group consisting of [Rh(C$_2$H$_4$)$_2$Cl]$_2$, [Rh(COD)$_2$][BF$_4$], and combination thereof. In another embodiment, the system further comprises a phosphorus ligand donor. In a further embodiment, the phosphorus ligand donor comprises tris(3,5-dimethylphenyl)phosphine.

In another further embodiment, the phosphorus ligand donor is selected from the group consisting of

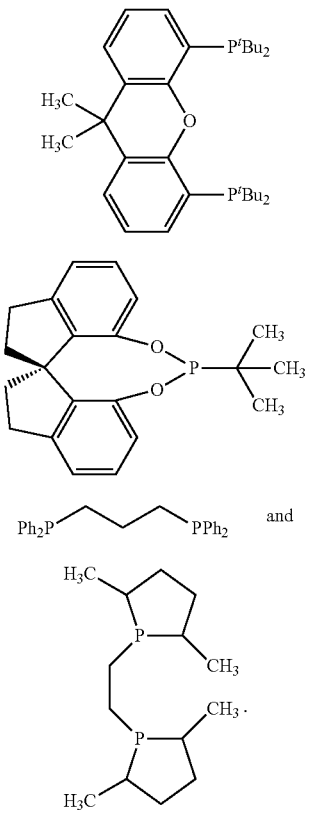

In another aspect, provided is a process for producing spinetoram, where the method uses the system provided herein at a temperature between 15° C. and 100° C. with a hydrogen gas pressure between 5 psig and 200 psig.

In another embodiment, the temperature is between 25° C. and 80° C.; between 25° C. and 50° C.; between 40° C. and 70° C.; or between 30° C. and 65° C. In another embodiment, the temperature is about 30° C., 45° C., or 65° C. In another embodiment, the hydrogen gas pressure is between 50 psig and 200 psig; between 60 psig and 150 psig; between 100 psig and 180 psig; or between 140 psig and 160 psig. In another embodiment, the hydrogen gas pressure is about 60 psig or 150 psig. In another embodiment, the yield of spinetoram is about or greater than 75%, 80%, 85%, 90%, or 95%. In another embodiment, the catalyst loading is between 0.01 mol % and 2 mol %; between 0.05 mol % and 1 mol %; between 0.02 mol % and 0.1 mol %; or between 0.1 mol % and 0.5 mol %.

DETAILED DESCRIPTION OF THE INVENTION

Spinetoram is a mixture of 5,6-dihydro-3'-ethoxy spinosyn J (major component) and 3'-ethoxy spinosyn L. The mixture can be prepared by ethoxylating a mixture of spinosyn J and spinosyn L, followed by hydrogenation. Accordingly, spinetoram is a semi-synthetic spinosyn and a mixture of 50-90% (2R,3aR,5aR,5bS,9S,13S,14R,16aS,16bR)-2-(6-deoxy-3-O-ethyl-2,4-di-O-methyl-α-L-mannopyranosyloxy)-13-[(2R,5S,6R)-5-(dimethylamino)tetrahydro-6-methylpyran-2-yloxy]-9-ethyl-2,3,3a,4,5,5a,5b,6,9,10,11,12,13,14,16a,16b-hexadecahydro-14-methyl1H-as-indaceno[3,2-d]oxacyclododecine-7,15-dione, and 50-10% (2R,3aR,5aS,5bS,9S,13S,14R,16aS,16bS)-2-(6-deoxy-3-O-ethyl-2,4-di-O-methyl-α-L-mannopyranosyloxy)-13-[(2R,5S,6R)-5-(dimethylamino)tetrahydro-6-methylpyran-2-yloxy]-9-ethyl-2,3,3a,5a,5b,6,9,10,11,12,13,14,16a,16b-tetradec ahydro-4,14-dimethyl-1H-as-indaceno[3,2-d]oxacyclododecine-7,15-dione. The synthesis of the components of spinetoram is described in U.S. Pat. No. 6,001,981.

Provided are rhodium (Rh)-based catalysts, such as [Rh(C₂H₄)₂Cl]₂ or [Rh(COD)₂][BF₄], with or without a phosphorus donor ligand, which are highly active and selective in the hydrogenation of Et J/L to spinetoram and are useful for methods of spinetoram production. In some embodiments, the methods and/or systems provided herein can achieve unexpectedly high yields, such as greater than 90%, at catalyst loadings lower than 0.1 mol %. In some embodiments, several such catalyst systems can deliver quantitative yields of spinetoram using one tenth the loading of traditional palladium on carbon (Pd/C) catalysts. The Rh catalysts, methods, and systems provided herein differ from previous methodologies in the catalysts and conditions used. Furthermore, the Rh catalysts, methods, and systems provided herein can be used at significantly lower catalyst loadings than current commercial loadings, which will improve process economics. Additional advantages of the Rh catalysts, methods, and systems provided herein as compared to previous methodologies include at least one of the following: (1) maintaining selectivity; (2) a higher turnover number (denoted TON); and (3) relatively insensitive to the quality and/or quantity of the starting material.

All patents and patent applications cited in this document are hereby incorporated by reference in their entireties.

Those skilled in the art would understand certain variations can exist based on the disclosure provided. Thus, the following examples are given for the purpose of illustrating the invention and shall not be construed as being a limitation on the scope of the invention or claims.

EXAMPLES

Example 1

Selective hydrogenation of 3'-O-ethyl-spinosyn J/L (Et J/L) mixture using [Rh(C₂H₄)₂Cl]₂—[Rh(C₂H₄)₂Cl]₂ (0.1019 grams (g), 0.2620 millimoles (mmol)) is added to a 10 mL volumetric flask, and the flask is diluted to the mark with tetrahydrofuran (THF). The catalyst stock solution is stirred to produce a dark brown, homogeneous mixture. An aliquot of the stock solution (0.500 milliliters (mL)) is added to a solution of Et J/L (8.15 g Et J, 0.0109 moles (mol) Et J and 2.64 g Et L, 0.00348 mol Et L) dissolved in isopropyl alcohol (IPA; 39.5 mL), and the mixture is stirred and then charged to a Parr reactor using a gas tight syringe. The reactor is heated to 30° C. and then pressurized to 60 psig with hydrogen gas. After 4.5 hours, the reactor is vented. By ¹H nuclear magnetic resonance (NMR) spectroscopic analysis, 0 g Et J (100% conversion), 8.011 g 175 Et J (98% yield) and 2.64 g Et L (100% yield) are found (TON=404 mol Et J/mol Rh).

Example 2

Selective hydrogenation of 3'-O-ethyl-spinosyn J/L (Et J/L) mixture using [Rh(COD)₂][BF₄]—[Rh(COD)₂][BF₄]

(0.0175 g, 0.0431 mmol) is dissolved in 40 mL methyl alcohol in a 50 mL jar. Purified Et J/L powder (8.3 g, 0.0111 mol Et J/L) is weighed into a 50 mL volumetric flask, and the flask is diluted to the mark with IPA. Once the Et J/L is dissolved, an aliquot (0.5 mL) of the yellow catalyst stock solution is combined with an aliquot of Et J/L stock solution (2.0 mL) and IPA (2.5 mL). The reaction mixture is charged to a glass test tube in a Freeslate Parallel Pressure Reactor (PPR). The reactor is heated to 65° C. and pressurized to 150 psig with hydrogen gas. After four hours, the reactor is cooled to room temperature and vented. By high-performance liquid chromatography (HPLC) analysis, 0.225 g Et J (19.9% conversion) and 0.0721 g Et L (99% yield) are found (TON=172 mol Et J/mol Rh).

Example 3

Selective hydrogenation of 3'-O-ethyl-spinosyn J/L (Et J/L) mixture using [Rh(COD)$_2$][BF$_4$] and tris(3,5-dimethylphenyl)phosphine —[Rh(COD)$_2$][BF$_4$] (0.0215 g, 0.0529 mmol) and tris(3,5-dimethylphenyl)phosphine (0.0383 g, 0.1106 mmol) (used as a phosphorus ligand donor) are weighed into a 5 mL volumetric flask, and the flask is diluted to the mark with methyl alcohol. The catalyst stock solution is stirred to produce an orange, homogeneous mixture. An aliquot of the catalyst stock solution (0.500 mL) is added to a solution of Et J/L (4.19 g Et J, 5.62 mmol Et J and 1.36 g Et L, 1.79 mmol Et L) dissolved in IPA (19.5 mL) and, the mixture is stirred and then charged to a Parr reactor using a gas tight syringe. The reactor is heated to 45° C. and then pressurized to 150 psig with hydrogen gas. After eight hours, the reactor is cooled to room temperature and vented. By $^1$H NMR analysis, 0.124 g Et J (97% conversion) and 1.32 g Et L (98% yield) are found (TON=1035 mol Et J/mol Rh).

Example 4

In a nitrogen-purged glovebox, a catalyst stock solution is prepared by stirring [Rh(C$_2$H$_4$)Cl]$_2$ and a phosphorus ligand in benzene or tetrahydrofuran (THF). 6 mL glass tubes are charged with a stock solution of Et J/L feed, Rh catalyst stock solution, biphenyl internal standard and IPA solvent. The reaction mixtures are heated to 65° C. and pressurized to 150 psi H$_2$. After four hours, the reaction mixtures are cooled to room temperature and vented. The reaction mixtures are analyzed using a calibrated 1260 Infinity HPLC, and results are shown in Table 1.

TABLE 1

| Ligand | Rh Source | % Et J Conversion | % Selectivity |
|---|---|---|---|
| L31 | [Rh(C$_2$H$_4$)$_2$Cl]$_2$ | 99% | 96% |
| L27 | [Rh(C$_2$H$_4$)$_2$Cl]$_2$ | 99% | 93% |
| L23 | [Rh(C$_2$H$_4$)$_2$Cl]$_2$ | 99% | 93% |
| L16 | [Rh(C$_2$H$_4$)$_2$Cl]$_2$ | 99% | 96% |

L31

TABLE 1-continued

| Ligand | Rh Source | % Et J Conversion | % Selectivity |
|---|---|---|---|

L16

Ph$_2$P⁀⁀⁀PPh$_2$

L23

L27

I claim:

1. A process for producing spinetoram comprising:

selectively hydrogenating a mixture of 3'-O-ethyl spinosyn J and 3'-O-ethyl spinosyn L, in the presence of (a) a homogeneous catalyst selected from the group consisting of [Rh(C$_2$H$_4$)$_2$Cl]$_2$, [Rh(COD)$_2$][BF$_4$], [Rh(COD)$_2$][OTs], and combinations thereof, at a temperature between 15° C. and 100° C. with a hydrogen gas pressure between 5 psig and 200 psig, wherein the COD is 1,5-cyclooctadiene and the OTs is p-toluenesulfonate; and (b) a phosphorus ligand donor selected from the group consisting of tris(3,5-dimethylphenyl)phosphine,

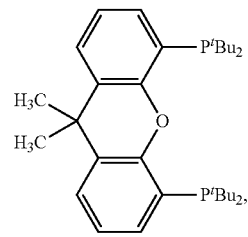

(L31)

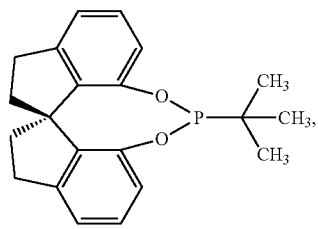

(L16)

-continued

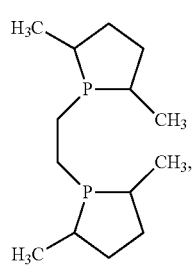 (L27)

and combinations thereof.

2. The process of claim 1, wherein the phosphorus ligand donor comprises tris(3,5-dimethylphenyl)phosphine.

3. The process of claim 1, wherein the phosphorus ligand donor is selected from the group consisting of

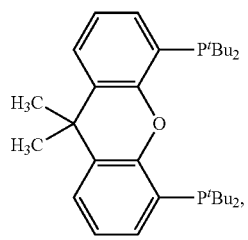 (L31)

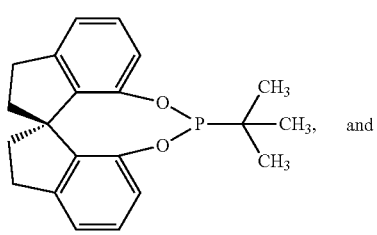 (L16)

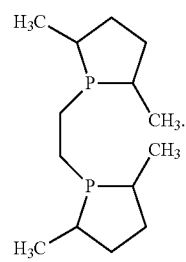 (L27)

4. The process of claim 1, wherein the temperature is about 30° C., 45° C., or 65° C.

5. The process of claim 1, wherein the hydrogen gas pressure is about 60 psig or 150 psig.

6. The process of claim 1, wherein the yield of spinetoram is about or greater than 90% by $^1$H nuclear magnetic resonance (NMR) spectroscopic analysis or high-performance liquid chromatography (HPLC) analysis.

7. The process of claim 1, wherein the catalyst loading is between 0.01 mol % and 2 mol %.

8. The process of claim 1, wherein the homogeneous catalyst is [Rh(C$_2$H$_4$)$_2$Cl]$_2$.

9. A selective hydrogenation system for producing spinetoram comprising
   (a) a mixture of 3'-O-ethyl spinosyn J and 3'-O-ethyl spinosyn L;
   (b) a homogeneous catalyst selected from the group consisting of [Rh(C$_2$H$_4$)$_2$Cl]$_2$, [Rh(COD)$_2$][BF$_4$], [Rh(COD)$_2$][OTs], and combinations thereof, wherein the COD is 1,5-cyclooctadiene and the OTs is p-toluenesulfonate: and
   (c) a phosphorus ligand donor selected from the group consisting of tris(3,5-dimethylphenyl) phosphine,

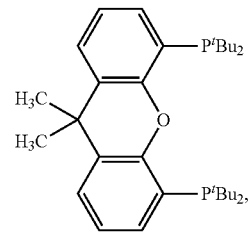 (L31)

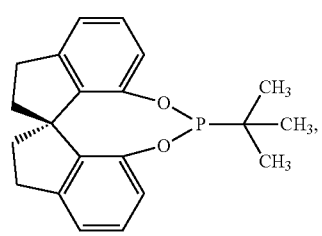 (L16)

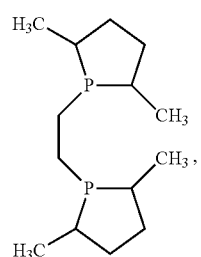 (L27)

and combinations thereof.

10. The system of claim 9, wherein the phosphorus ligand donor comprises tris(3,5-dimethylphenyl)phosphine.

11. The system of claim 9, wherein the phosphorus ligand donor is selected from the group consisting of

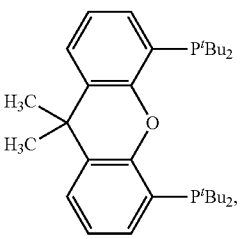 (L31)

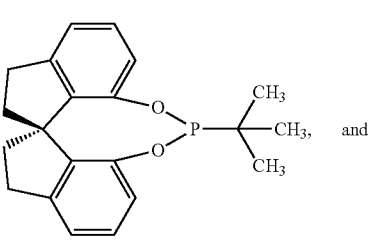 (L16)

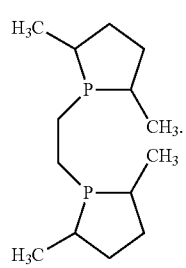
(L27)

12. A process for producing spinetoram comprising providing the system of claim 9 to hydrogenate the mixture of 3-O-enthyl spinosyn J and 3'-O-ethyl spinosyn L at a temperature between 15° C. and 100° C. with a hydrogen gas pressure between 5 psig and 200 psig.

13. The process of claim 12, wherein the yield of spinetoram is about or greater than 90% by $^1$H nuclear magnetic resonance (NMR) spectroscopic analysis or high-performance liquid chromatography (HPLC) analysis.

14. The process of claim 12, wherein the catalyst loading is between 0.01 mol % and 2 mol %.

* * * * *